United States Patent
Abramovici et al.

(10) Patent No.: US 6,893,659 B2
(45) Date of Patent: May 17, 2005

(54) PHARMACEUTICAL COMPOSITION FOR ORAL ADMINISTRATION OF A N-PIPERIDINO-3- PYRAZOLECARBOXAMIDE DERIVATIVE, ITS SALTS AND THEIR SOLVATES

(75) Inventors: Bernard Abramovici, Juvignac (FR); Christian Condamine, Fabregues (FR); Jean-Claude Gromenil, Montbazin (FR)

(73) Assignee: Sanoti-Synthelabo, Paris (FR)

( * ) Notice: Subject to any disclaimer, the term of this patent is extended or adjusted under 35 U.S.C. 154(b) by 0 days.

(21) Appl. No.: 10/136,148

(22) Filed: May 1, 2002

(65) Prior Publication Data

US 2003/0003145 A1 Jan. 2, 2003

Related U.S. Application Data

(63) Continuation of application No. 09/381,706, filed as application No. PCT/FR98/00631 on Mar. 27, 1998, now abandoned.

(30) Foreign Application Priority Data

Mar. 28, 1997 (FR) .......................................... 97 03835

(51) Int. Cl.$^7$ ................................................. A61K 9/20
(52) U.S. Cl. ....................... 424/464; 424/489; 514/614; 514/960
(58) Field of Search ................................. 424/456, 464, 424/465, 470, 474, 479, 489, 499; 514/614, 960

(56) References Cited

U.S. PATENT DOCUMENTS

| | | | | |
|---|---|---|---|---|
| 3,951,821 A | * | 4/1976 | Davidson | .................. 252/1 |
| 5,087,454 A | | 2/1992 | Duerholz et al. | |
| 5,624,941 A | * | 4/1997 | Barth et al. | ................. 514/326 |
| 5,725,883 A | * | 3/1998 | Staniforth et al. | .......... 424/489 |

FOREIGN PATENT DOCUMENTS

| | | |
|---|---|---|
| EP | 656354 | 6/1995 |
| WO | WO 96/22080 | 7/1996 |

OTHER PUBLICATIONS

M. Rinaldi–Carmona et al., FEBS Letters, 1994, pp. 240–244.

* cited by examiner

*Primary Examiner*—Gary Kunz
*Assistant Examiner*—Konata M. George
(74) *Attorney, Agent, or Firm*—Michael D. Alexander; Balaram Gupta

(57) ABSTRACT

The pharmaceutical compositions for oral administration according to the invention contain 0.5% to 20% of N-piperidino-5-(4-chlorophenyl)-1-(2,4-dichlorophenyl)-4-methylpyrazole-3-carboxamide in microcrystalline form, and pharmaceutical excipients; they are formulated by wet granulation.

13 Claims, No Drawings

PHARMACEUTICAL COMPOSITION FOR ORAL ADMINISTRATION OF A N-PIPERIDINO-3- PYRAZOLECARBOXAMIDE DERIVATIVE, ITS SALTS AND THEIR SOLVATES

CROSS REFERENCE TO RELATED APPLICATIONS

This application is a continuation of prior application Ser. No. 09/381,706, filed Sep. 22, 1999, now abandoned which in turn is a 35 U.S.C. §371 application of PCT International application No. PCT/FR98/00631, filed Mar. 27, 1998, which in turn claims priority from French application No. 97/03835, filed Mar. 28, 1997.

The present invention relates to a pharmaceutical composition for the oral administration of N-piperidino-5-(4-chlorophenyl)-1-(2,4-dichlorophenyl)-4-methylpyrazole-3-carboxamide of the formula

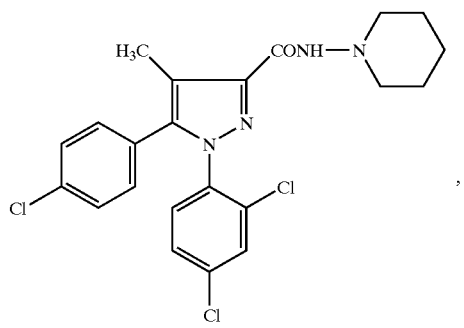

its pharmaceutically acceptable salts and their solvates, which are hereafter referred to as compounds of formula (I).

The compounds of formula (I) and their method of preparation are described in European patent application EP 656 354.

N-Piperidino-5-(4-chlorophenyl)-1-(2,4-dichlorophenyl)-4-methylpyrazole-3-carboxamide, which is also known by the code name SR 141716 and is called compound A in the following description, is very particularly preferred for the pharmaceutical composition according to the present invention.

The pharmacological properties of the compounds of formula (I), which are selective antagonists of the CB1 central cannabinoid receptors, have been recorded, especially in the publication of M. Rinaldi-Carmona et al., FEBS Letters, 1994, 240–244.

The oral administration of such compounds requires them to have a good absorption, which entails both a good solubility in aqueous media and a good ability to pass through the intestinal membrane (M. Rowland and T. N. Tozer in Clinical Pharmacokinetics, concepts and applications, published by Lea and Fehiger, 1989, 2nd edition, pp. 113–130).

The permeability of the epithelium of the compounds is evaluated using the Caco-2 cell line, which has the characteristic of undergoing differentiation in vitro to form an epithelial monolayer (Crit. Rev. Ther. Drug Carrier System, 1991, 8 (4), 105–330). In this model the permeability of compound A dissolved in dimethyl sulfoxide (DMSO) is high, showing that it has a good ability to be absorbed by the intestine when it is in solution.

Furthermore, the hydrophobic character of the compounds of formula (I) is very strongly pronounced. Thus it has been observed that compound A is not wettable in water and that this compound and its salts are practically insoluble in water, irrespective of the pH. These compounds are soluble in alcohols and glycols and more particularly in polyethylene glycols (PEG).

However, when the solutions obtained with an alcohol or a glycol are diluted in an aqueous medium, the compound of formula (I) precipitates because of its strongly hydrophobic character.

The compounds of formula (I), and particularly compound A, are not very electrostatic. Micronization can be carried out with a good yield (about 85%) and affords particles of about 1 micron. Analytical controls performed after micronization show that there is no modification of the crystalline form.

On studying the wettability, it was found that the rate of penetration of water into a bed of powder formulated by wet granulation is much higher than that measured in a bed of powder obtained by dry mixing. A study of the effects of incorporating wetting agents showed that a low concentration of a sodium alkylsulfate considerably increases the wettability.

It was further found that the presence of a disintegrating agent, such as crosslinked sodium carboxymethyl cellulose, in the formulation makes it possible to improve the kinetics of dissolution.

Surprisingly it was found that by associating a sodium alkylsulfate with a disintegrating agent in the same formulation, the formulation dissolves rapidly and completely and with a good reproducibility of the results.

Thus, according to one of its aspects, the present invention relates to a pharmaceutical composition for the oral administration of a compound of formula (I), comprising:
 0.5% to 20% by weight of a compound of formula (I) in micronized form,
 0.05% to 0.5% by weight of a sodium alkylsulfate,
 2.5% to 10% by weight of disintegrating agent,
 and pharmaceutical excipients,
said composition being formulated by wet granulation.

Wet granulation is understood as meaning the pharmaceutical operation by which a mixture of powders containing the active principle can be densified with the aid of a granulating liquid, said mixture constituting the internal phase of the formulation, the resulting wet mass being dried and then graded before the ingredients constituting the external phase of said formulation are added.

According to the present invention, sodium alkylsulfate is understood as meaning a sodium ($C_8$–$C_{12}$)alkylsulfate, for example sodium octylsulfate or, preferably, sodium laurylsulfate.

According to the present invention, disintegrating agent is understood as meaning cellulose or cellulose derivatives such as sodium carboxymethyl cellulose or crosslinked sodium carboxymethyl cellulose, crospovidone, pregelatinized starch or sodium carboxymethyl starch, crosslinked sodium carboxymethyl cellulose being a preferred disintegrating agent.

The pharmaceutical compositions according to the present invention can be presented in the form of gelatin capsules, tablets, sachets or powders, preferably in the form of gelatin capsules.

The pharmaceutical excipients which can be used for the pharmaceutical composition according to the present invention include especially a diluent, a binder and a lubricant. A flowing agent, an antiadhesive and, optionally, a coloring agent and/or a flavoring agent can also be added.

The diluent used in the composition of the present invention can be one or more compounds which are capable of densifying the active principle to give the desired mass. The preferred diluents are inorganic phosphates such as calcium phosphates; sugars such as hydrated or anhydrous lactose, or mannitol; and cellulose or cellulose derivatives such as, for example, microcrystalline cellulose, starch, corn starch or pregelatinized starch. Lactose monohydrate, mannitol, microcrystalline cellulose and corn starch, used by themselves or in a mixture, for example a mixture of lactose monohydrate and corn starch, are very particularly preferred.

The binder employed in the composition of the present invention can be one or more compounds which are capable of densifying a compound of formula (I) by converting it to larger and denser particles with better flow properties. The preferred binders are alginic acid or sodium alginate; cellulose and cellulose derivatives such as sodium carboxymethyl cellulose, ethyl cellulose, hydroxyethyl cellulose, hydroxypropyl cellulose, hydroxypropyl methyl cellulose or methyl cellulose; gelatin; acrylic acid polymers; and povidone, for example povidone K 30, which is a very particularly preferred binder. The binder is present in a proportion of 1% to 10% by weight in the pharmaceutical composition according to the invention.

The lubricant employed in the composition of the present invention can be one or more compounds which are capable of preventing the problems associated with the preparation of dry forms, such as the sticking and/or seizing problems which occur in the machines during compression or filling. The preferred lubricants are fatty acids or fatty acid derivatives such as calcium stearate, glyceryl monostearate, glyceryl palmitostearate, magnesium stearate, sodium laurylsulfate, sodium stearylfumarate, zinc stearate or stearic acid; hydrogenated vegetable oils, for example hydrogenated castor oil; polyalkylene glycols, especially polyethylene glycol; sodium benzoate; or talcum. Magnesium stearate is preferred according to the present invention. The lubricant is present in a proportion of 0.2% to 5% by weight in the pharmaceutical composition according to the invention.

The antiadhesive which may be employed in the composition of the present invention can be one or more compounds which are capable of reducing the sticky character of the formulation, for example of preventing adhesion to metal surfaces. The preferred antiadhesives are compounds containing silicon, for example silica or talcum. The antiadhesive can be present in a proportion of 0 to 5% by weight in the pharmaceutical composition according to the invention.

The flowing agent which may be employed in the composition of the present invention can be one or more compounds which are capable of facilitating the flow of the prepared formulation. The preferred flowing agents are compounds containing silicon, for example anhydrous colloidal silica or precipitated silica. The flowing agent can be present in a proportion of 0 to 15% by weight in the pharmaceutical composition according to the invention.

According to the present invention, the pharmaceutical compositions are prepared by a wet granulation process. Thus, for the internal phase, the active principle, the diluent, the binder, the disintegrating agent, the sodium alkylsulfate and, optionally, the coloring agent are mixed at room temperature and then wetted with the granulating liquid. The wet mass obtained is dried and then graded. The ingredient or ingredients of the external phase, namely the lubricant, possibly the antiadhesive, the flowing agent and, if appropriate, the coloring agent and/or the flavoring agent, are then added to the graded dry grains.

Purified water is used as the granulating liquid.

In one preferred embodiment, the sodium alkylsulfate is added to the purified water in order to carry out the wet granulation.

In particular, the present invention relates to a pharmaceutical composition for oral administration which comprises:
    0.5% to 20% by weight of compound A in micronized form,
    0.05% to 0.5% by weight of sodium laurylsulfate,
    2.5% to 10% by weight of crosslinked sodium carboxymethyl cellulose,
    and pharmaceutical excipients,
said composition being formulated by wet granulation.

Preferably the present invention relates to a pharmaceutical composition for oral administration which is formulated by wet granulation and which contains:
    0.5% to 20% by weight of compound A in micronized form,
    0.1% by weight of sodium laurylsulfate,
    5% by weight of crosslinked sodium carboxymethyl cellulose,
    1% to 10% by weight of binder,
    0.2% to 5% by weight of lubricant,
    and a diluent in sufficient amount for 100%.

Very particularly, the present invention relates to pharmaceutical compositions in the form of gelatin capsules which are prepared by wet granulation and which have one of the following formulations, expressed in percentages by weight:

| i) Internal phase | |
| --- | --- |
| micronized compound A | 0.59% |
| corn starch | 30% |
| 200 mesh lactose monohydrate | 60.78% |
| povidone K 30 | 2.53% |
| crosslinked sodium carboxymethyl cellulose | 5% |
| Granulation | |
| sodium laurylsulfate | 0.1% |
| purified water | QS |
| External phase | |
| magnesium stearate | 1% |
| ii) Internal phase | |
| micronized compound A | 5.88% |
| corn starch | 30% |
| 200 mesh lactose monohydrate | 55.49% |
| povidone K 30 | 2.53% |
| crosslinked sodium carboxymethyl cellulose | 5% |
| Granulation | |
| sodium laurylsulfate | 0.1% |
| purified water | QS |
| External phase | |
| magnesium stearate | 1% |
| iii) Internal phase | |
| micronized compound A | 17.64% |
| corn starch | 30% |
| 200 mesh lactose monohydrate | 43.73% |
| povidone K 30 | 2.53% |
| crosslinked sodium carboxymethyl cellulose | 5% |
| Granulation | |
| sodium laurylsulfate | 0.1% |
| purified water | QS |
| External phase | |
| magnesium stearate | 1% |

The characteristics and advantages of the compositions according to the invention will become appear in the light of the following description, from the compositions given as Examples.

Tests

1. Study of the Solubility of the Compounds of Formula (I)

The solubilities of the compounds of formula (I) are measured in different aqueous media. The instantaneous solubility is evaluated at room temperature by quantitative analysis. The results, expressed in μg per ml, are collated in Table 1 below:

TABLE 1

| Compound of formula (I) | Dissolution medium | | | |
|---|---|---|---|---|
| | Water | Water + 10% ethanol | Acetic buffer pH 7.5 | Phosphate buffer pH 7.5 |
| Compound A (base) | 1 | 1.2 | 1.9 | 1.6 |
| Hydrochloride (solvated) | 37 | 10 | 54 | 0.5 |
| Methanesulfonate (solvated) | 39 | 48 | 54 | 0.9 |
| Hydrogensulfate | 13 | 38 | 30 | 0.9 |
| Paratoluenesulfonate | 3.9 | 7.3 | 2.4 | 0.2 |
| Phosphate | 1.3 | 7.5 | 0.9 | 0.7 |
| Solvated compound A | 0.7 | 0.9 | 1.2 | 0.9 |

Measurements were also made of the solubility of compound A in different solvents (Table 2) and after dilution in water of the solutions formed (Table 3).

TABLE 2

| Solvent | Solubility of compound A |
|---|---|
| Ethanol | 35 mg/ml |
| Polyethylene glycol 400 | 50 mg/ml |
| Polyethylene glycol 1500 at 60° C. | 80 mg/g |

TABLE 3

| Solvent | Solubility of compound A | Dilution in water | Amount of compound A dissolved | |
|---|---|---|---|---|
| | | | theoretical | measured |
| Ethanol | 35 mg/ml | 10% | 3.5 mg/ml | $1.2 \cdot 10^{-3}$ mg/ml |
| Polyethylene glycol 400 | 50 mg/ml | 30% | 15 mg/ml | $3 \cdot 10^{-3}$ mg/ml |
| Polyethylene glycol 1500 at 60° C. | 80 mg/g | not dilutable | | |

2. Study of the Wettability

The wettability of compound A was studied in different formulations using the method of H. Mohamad et al., Labo Pharma. Problèmes techniques, 1984, 32 (346), 284–289.

2.1. Influence of the Granulation Process

A formulation obtained by simple mixing (formulation 1) was compared with a formulation obtained by wet granulation (formulation 2).

| Formulation 1 | |
|---|---|
| compound A | 30 mg |
| modified corn starch | 48 mg |
| extrafine crystals of lactose monohydrate | 70.1 mg |
| anhydrous colloidal silica | 0.4 mg |
| magnesium stearate | 1.5 mg |
| Gelatin capsule | 150 mg |

| Formulation 2 | |
|---|---|
| compound A | 30 mg |
| modified corn starch | 51 mg |
| 200 mesh lactose monohydrate | 83 mg |
| povidone K 30 | 4.3 mg |
| magnesium stearate | 1.7 mg |
| Gelatin capsule | 170 mg |

The wettability measured according to H. Mohamad's method is 22 $mg^2/s$ for formulation 1 and 10 $mg^2/s$ for formulation 2.

Thus the wet granulation process improves the wettability by a factor of 5.

2.2. Influence of the Active Principle Content

For comparison purposes, formulations in which the active principle content was respectively 10 mg (formulation 3) and 1 mg (formulation 4) were prepared by wet granulation.

TABLE 4

| | Formulation 3 | Formulation 4 |
|---|---|---|
| compound A | 10 mg | 1 mg |
| corn starch | 51 mg | 51 mg |
| 200 mesh lactose monohydrate | 103 mg | 112 mg |
| povidone K 30 | 4.3 mg | 4.3 mg |
| magnesium stearate | 1.7 mg | 1.7 mg |
| Gelatin capsule | 170 mg | 170 mg |

The wettability is 500 $mg^2/s$ for formulation 3.
The wettability is 1000 $mg^2/s$ for formulation 4.

Thus the wettability is inversely proportional to the amount of active principle contained in the formulation. This illustrates the hydrophobic character of compound A.

2.3. Influence of the Excipients

Several formulations were prepared by wet granulation and compared with a reference formulation also obtained by wet granulation.

TABLE 5

| | Formulation | | | |
|---|---|---|---|---|
| | 4 | 5 | 6 | 7 |
| compound A | 30 | 30 | 30 | 30 | 30 |
| corn starch | 51 | 51 | 51 | 51 | 51 |
| 200 mesh lactose monohydrate | 83 | 83 | 83 | 83 | 83 |
| povidone K 30 | 4.3 | 4.3 | 4.3 | 4.3 | 4.3 |
| sodium laurylsulfate | | 0.17 | 0.85 | | |
| polyethylene glycol 6000 | | | | 1.7 | 8.5 |
| magnesium stearate | | 1.7 | 1.7 | 1.7 | 1.7 |
| wettability $mg^2/s$ | 600 ±150 | 1200 ±300 | 2300 ±300 | 1100 ±200 | 1100 ±200 |

Only 0.5% sodium laurylsulfate improves the wettability significantly.

The wettability measurements are not suitable for studying the effect of a disintegrating agent like crosslinked sodium carboxymethyl cellulose.

3. Study of the Dissolution in a Gastric Medium

The kinetics of dissolution of different formulations in a gastric medium were studied at 37° C. in a phosphate-citrate buffer of pH 3 for 30 minutes.

When 40 mg of compound A are placed in one liter of the dissolution medium with nothing else added, it is observed that no dissolution takes place.

To enable dissolution of the test formulations, 0.2% of sodium laurylsulfate was added to the medium as a surfactant.

TABLE 6

| Formulation | A mg | B mg | C mg | D mg |
|---|---|---|---|---|
| Internal phase | | | | |
| compound A | 30.0 | 30.0 | 30.0 | 30.0 |
| corn starch | 51.0 | 51.0 | 51.0 | 51.0 |
| 200 mesh lactose monohydrate | 83.0 | 83.0 | 83.0 | 83.0 |
| povidone K 30 | 4.3 | 4.3 | 4.3 | 4.3 |
| sodium laurylsulfate | 0.17 | 0.85 | | |
| polyethylene glycol 6000 | | | 1.7 | 8.5 |
| crosslinked sodium carboxymethyl cellulose | | | | |
| purified water for wetting | QS | QS | QS | QS |
| External phase | | | | |
| magnesium stearate | 1.7 | 1.7 | 1.7 | 1.7 |
| content of the gelatin capsule | 170.17 mg | 170.85 mg | 171.7 mg | 178.5 mg |

| Formulation | E mg | F mg | G mg |
|---|---|---|---|
| Internal phase | | | |
| compound A | 30.0 | 30.0 | 30.0 |
| corn starch | 51.0 | 51.0 | 51.0 |
| 200 mesh lactose monohydrate | 83.0 | 83.0 | 83.0 |
| povidone K 30 | 4.3 | 4.3 | 4.3 |
| sodium laurylsulfate | | 0.17 | |
| polyethylene glycol 6000 | | | |
| crosslinked sodium carboxymethyl cellulose | 8.5 | 8.5 | 4.25 |
| purified water for wetting | QS | QS | QS |
| External phase | | | |
| magnesium stearate | 1.7 | 1.7 | 1.7 |
| content of the gelatin capsule | 178.5 mg | 178.67 mg | 174.25 mg |

6 tests were carried out for each formulation and the amount of compound A dissolved in the medium was measured every 5 minutes.

Table 7 indicates the mean value of the percentage of compound A dissolved and the standard deviation relative to this value for the different formulations described in Table 6.

TABLE 7

| Time in minutes | Compound A dissolved in % (standard deviation) | | | |
|---|---|---|---|---|
| | A | B | C | D |
| 5 | 63.4 (12.8) | 63.5 (24.6) | 56.3 (20.1) | 61.9 (17.0) |
| 10 | 87.9 (13.6) | 87.6 (13.5) | 76.2 (15.6) | 74.7 (15.6) |
| 15 | 97.6 (7.9) | 94.6 (9.7) | 86.9 (13.5) | 81.6 (16.0) |
| 20 | 100.7 (5.4) | 96.6 (7.7) | 93.8 (11.3) | 88.1 (16.0) |
| 25 | 102.1 (4.2) | 98.6 (5.6) | 97.8 (7.7) | 92.1 (15.2) |
| 30 | 103.0 (3.2) | 99.8 (3.7) | 100.2 (5.1) | 94.8 (14.2) |

| Time in minutes | Compound A dissolved in % (standard deviation) | | |
|---|---|---|---|
| | E | F | G |
| 5 | 62.1 (8.5) | 64.9 (6.4) | 69.8 (7.2) |
| 10 | 85.9 (10.0) | 96.7 (4.5) | 95.4 (8.8) |
| 15 | 97.6 (5.9) | 99.8 (2.3) | 100.4 (5.2) |
| 20 | 100.9 (2.8) | 100.7 (2.1) | 102.8 (2.8) |
| 25 | 101.6 (2.7) | 101.3 (1.9) | 103.8 (1.7) |
| 30 | 102.1 (2.8) | 101.7 (1.5) | 104.2 (1.6) |

For formulations C and D, which respectively contain 1% and 5% of polyethylene glycol 6000, it is found that the maximum dissolution is only reached after 30 minutes.

For formulations A and B, which respectively contain 0.1% and 0.5% of sodium laurylsulfate, it is observed that the maximum value is reached after 20 minutes and 30 minutes respectively.

Also, the measured results are scattered for each of formulations A, B, C and D.

The results observed with formulations E, F and G show the value of the presence of crosslinked sodium carboxymethyl cellulose in promoting the dissolution.

For formulations E and G, which respectively contain 5% and 2.5% of crosslinked sodium carboxymethyl cellulose, it is observed that 100% of compound A is dissolved after 20 minutes or 15 minutes respectively, and that the results are relatively scattered in the first 15 minutes.

Formulation F, which contains both 0.1% of sodium laurylsulfate and 5% of crosslinked sodium carboxymethyl cellulose, gives the best results. In fact, compound A is totally dissolved after 15 minutes; furthermore, the deviation between the results of the different tests is very low (deviation of 2.3 to 1.5 between 15 and 30 minutes).

5. Evaluation of the Intestinal Transepithelial Passage of Compound A

Caco-2 cells are cultured onto microporous polycarbonate filters covered with collagen. The cellular monolayer formed on the filter then makes it possible to separate an apical compartment (imitating the intestinal lumen) from a basal compartment (imitating the blood circulation).

The composition containing the compound to be studied is placed on the apical side and the passage of this compound, dispersed or solubilized in Hank's medium, through this cellular barrier is evaluated by measuring the kinetics of its appearance on the basal side. This aqueous medium, of pH 6.5, has the following composition: $NaCl = 8.0$ g/l; $KCl = 0.4$ g/l; $CaCl_2 = 0.19$ g/l; $MgCl_2 = 0.1$ g/l; $MgSO_4 = 0.1$ g/l; $Na_2HPO_4 = 0.09$ g/l; $KH_2PO_4 = 0.06$ g/l; $NaHCO_3 = 0.35$ g/l; glucose = 1 g/l; phenol red = 0.01 g/l.

The coefficient of permeability P, in cm/s, is then determined; this characterizes the rate of passage of the molecule through the membrane, namely:

$$P = (da/dt) \cdot (1/A \cdot Co)$$

where:

da/dt = variation of the amount of test compound passing through the cellular monolayer as a function of time (mol/s)

A = surface area of the monolayer ($cm^2$)

Co = initial concentration of the test compound (mol/l)

3.1. Coefficient of Permeability of Compound A, Introduced in Hank's Medium, in Solution in DMSO $$P = 96 \cdot 10^{-7} \text{ cm/s}$$

The permeability of compound A measured in this way in solution (in DMSO) indicates an intrinsic characteristic of this compound. This result indicates the very good ability of compound A to pass through the epithelium when it is in solution.

3.2. Relative Rate of Intestinal Transepithelial Passage of Compound A

The rate of passage of compound A in formulation X was measured and compared with that of compound A in suspension.

| Formulation X | |
| --- | --- |
| compound A | 30 mg |
| modified corn starch | 51 mg |
| 200 mesh lactose monohydrate | 83 mg |
| povidone K 30 | 4.3 mg |
| sodium laurylsulfate | 0.17 mg |
| crosslinked sodium carboxymethyl cellulose | 8.5 mg |
| magnesium stearate | 1.7 mg |
| Gelatin capsule | 178.67 mg |

| Formulation of compound A | Relative rate of passage |
| --- | --- |
| Compound A in suspension in Hank's medium | 1 |
| Compound A formulated in X | 7 |

EXAMPLE 1

1 mg Gelatin Capsule

A gelatin capsule prepared by wet granulation and having the following composition:

| Internal phase | |
| --- | --- |
| micronized compound A | 1 mg |
| corn starch | 51 mg |
| 200 mesh lactose monohydrate | 103.33 mg |
| povidone K 30 | 4.3 mg |
| crosslinked sodium carboxymethyl cellulose | 8.5 mg |
| Granulation | |
| sodium laurylsulfate | 0.17 mg |
| purified water | QS |
| External phase | |
| magnesium stearate | 1.7 mg |
| For a size 3 white-opaque gelatin capsule completed up to | 170 mg |

EXAMPLE 2

10 mg Gelatin Capsule

A gelatin capsule prepared by wet granulation and having the following composition:

| Internal phase | |
| --- | --- |
| micronized compound A | 10 mg |
| corn starch | 51 mg |
| 200 mesh lactose monohydrate | 94.33 mg |
| povidone K 30 | 4.3 mg |
| crosslinked sodium carboxymethyl cellulose | 8.5 mg |
| Granulation | |
| sodium laurylsulfate | 0.17 mg |
| purified water | QS |
| External phase | |
| magnesium stearate | 1.7 mg |
| For a size 3 white-opaque gelatin capsule completed up to | 170 mg |

EXAMPLE 3

30 mg Gelatin Capsule

A gelatin capsule prepared by wet granulation and having the following composition:

| Internal phase | |
| --- | --- |
| micronized compound A | 30 mg |
| corn starch | 51 mg |
| 200 mesh lactose monohydrate | 74.33 mg |
| povidone K 30 | 4.3 mg |
| crosslinked sodium carboxymethyl cellulose | 8.5 mg |
| Granulation | |
| sodium laurylsulfate | 0.17 mg |
| purified water | QS |
| External phase | |
| magnesium stearate | 1.7 mg |
| For a size 3 white-opaque gelatin capsule completed up to | 170 mg |

EXAMPLE 4

30 mg Gelatin Capsule

A gelatin capsule prepared by wet granulation and having the following composition:

| Internal phase | |
| --- | --- |
| micronized compound A | 30 mg |
| corn starch | 51 mg |
| 200 mesh lactose monohydrate | 73.65 mg |
| povidone K 30 | 4.3 mg |
| crosslinked sodium carboxymethyl cellulose | 8.5 mg |
| Granulation | |
| sodium laurylsulfate | 0.85 mg |
| purified water | QS |
| External phase | |
| magnesium stearate | 1.7 mg |
| For a size 3 white-opaque gelatin capsule completed up to | 170 mg |

EXAMPLE 5

1 mg Tablet

| Internal phase | |
| --- | --- |
| micronized compound A | 1 mg |
| corn starch | 50 mg |
| 200 mesh lactose monohydrate | 130 mg |
| 6 cP hydroxypropyl methyl cellulose | 6 mg |
| crosslinked sodium carboxymethyl cellulose | 10 mg |
| Granulation | |
| sodium laurylsulfate | 1 mg |
| purified water | QS |
| External phase | |
| magnesium stearate | 2 mg |
| For a tablet completed up to | 200 mg |

EXAMPLE 6

10 mg Tablet

| Internal phase | |
|---|---|
| micronized compound A | 10 mg |
| corn starch | 50 mg |
| 200 mesh lactose monohydrate | 211.5 mg |
| 6 cP hydroxypropyl methyl cellulose | 9 mg |
| sodium carboxymethyl starch | 15 mg |
| sodium laurylsulfate | 1.5 mg |
| Granulation | |
| purified water | QS |
| External phase | |
| magnesium stearate | 3 mg |
| For a tablet completed up to | 300 mg |

EXAMPLE 7

30 mg Tablet

| Internal phase | |
|---|---|
| micronized compound A | 30 mg |
| corn starch | 80 mg |
| 200 mesh lactose monohydrate | 252 mg |
| povidone K 30 | 12 mg |
| crosslinked sodium carboxymethyl cellulose | 20 mg |
| sodium laurylsulfate | 2 mg |
| Granulation | |
| purified water | QS |
| External phase | |
| magnesium stearate | 4 mg |
| For a tablet completed up to | 400 mg |

What is claimed is:

1. A pharmaceutical composition for the oral administration of N-piperidino-5-(4-chlorophenyl)-1-(2,4-dichlorophenyl)-4-methylpyrazole-3-carboxamide of the formula

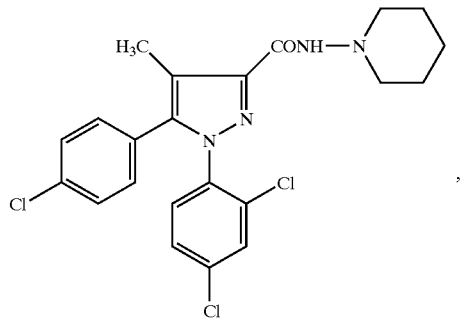

one of its pharmaceutically acceptable salts or one of their solvates (active principle hereafter), comprising:
 0.5% to 20% by weight of active principle in micronized form,
 0.05% to 0.5% by weight of sodium laurylsulfate,
 2.5% to 10% by weight of a crosslinked sodium carboxymethyl cellulose disintegrating agent, and pharmaceuticals excipients, said composition being formulated by wet granulation wherein said sodium alkylsulfate and said disintegrating agent are added as separate ingredients.

2. A pharmaceutical composition according to claim 1 which contains:
 0.5% to 20% by weight of N-piperidino-5-(4-chlorophenyl)-1-(2,4-dichlorophenyl)-4-methylpyrazole-3-carboxamide in micronized form,
 0.1% by weight of sodium laurylsulfate,
 5% by weight of crosslinked sodium carboxymethyl cellulose,
 1% to 10% by weight of binder,
 0.2% to 5% by weight of lubricant,
 and a diluent in a sufficient amount for 100%.

3. A pharmaceutical composition according to claim 1 in the form of a gelatin capsule and having the following formulation, expressed in percentages by weight:

| Internal phase | |
|---|---|
| N-piperidino-5-(4-chlorophenyl)-1-(2,4-dichlorophenyl)-4-methylpyrazole-3-carboxamide in micronized form | 0.59% |
| corn starch | 30% |
| 200 mesh lactose monohydrate | 60.78% |
| povidone K 30 | 2.53% |
| crosslinked sodium carboxymethyl cellulose | 5% |
| Granulation | |
| sodium laurylsulfate | 0.1% |
| water | QS |
| External phase | |
| magnesium stearate | 1%. |

4. A pharmaceutical composition according to claim 1 in the form of a gelatin capsule and having the following formulation, expressed in percentages by weight:

| Internal phase | |
|---|---|
| N-piperidino-5-(4-chlorophenyl)-1-(2,4-dichlorophenyl)-4-methylpyrazole-3-carboxamide in micronized form | 5.88% |
| corn starch | 30% |
| 200 mesh lactose monohydrate | 55.49% |
| povidone K 30 | 2.53% |
| crosslinked sodium carboxymethyl cellulose | 5% |
| Granulation | |
| sodium laurylsulfate | 0.1% |
| water | QS |
| External phase | |
| magnesium stearate | 1%. |

5. A pharmaceutical composition according to claim 1 in the form of a gelatin capsule and having the following formulation, expressed in percentages by weight:

| Internal phase | |
|---|---|
| N-piperidino-5-(4-chlorophenyl)-1-(2,4-dichlorophenyl)-4-methylpyrazole-3-carboxamide in micronized form | 17.64% |
| corn starch | 30% |
| 200 mesh lactose monohydrate | 43.73% |
| povidone K 30 | 2.53% |
| crosslinked sodium carboxymethyl cellulose | 5% |

-continued

| Granulation | |
|---|---|
| sodium laurylsulfate | 0.1% |
| water | QS |
| External phase | |
| magnesium stearate | 1%. |

6. A process for the preparation of a pharmaceutical composition according to claim 1 wherein:

a) the active principle, the disintegrating agent and the sodium alkylsulfate are mixed at room temperature with a diluent, a binder and, optionally, a coloring agent;

b) the mixture is wetted with purified water;

c) the resulting wet mass is dried and graded; and d) a lubricant and, optionally, an antiadhesive, a flowing agent, a coloring agent and/or a flavoring agent are added to the resulting graded dry grains.

7. A process according to claim 6 for the preparation of a pharmaceutical composition in the form of a gelatin capsule and having the following formulation, expressed in percentages by weight:

| Internal phase | |
|---|---|
| N-piperidino-5-(4-chlorophenyl)-1-(2,4-dichlorophenyl)-4-methylpyrazole-3-carboxamide in micronized form | 0.59% |
| corn starch | 30% |
| 200 mesh lactose monohydrate | 60.78% |
| povidone K 30 | 2.53% |
| crosslinked sodium carboxymethyl cellulose | 5% |
| Granulation | |
| sodium laurylsulfate | 0.1% |
| water | QS |
| External phase | |
| magnesium stearate | 1% |
| wherein the sodium alkylsulfate is incorporated in step b). | |

8. A process according to claim 6 for the preparation of a pharmaceutical composition in the form of a gelatin capsule and having the following formulation, expressed in percentages by weight:

| Internal phase | |
|---|---|
| N-piperidino-5-(4-chlorophenyl)-1-(2,4-dichlorophenyl)-4-methylpyrazole-3-carboxamide in micronized form | 5.88% |
| corn starch | 30% |
| 200 mesh lactose monohydrate | 55.49% |
| povidone K 30 | 2.53% |
| crosslinked sodium carboxymethyl cellulose | 5% |
| Granulation | |
| sodium laurylsulfate | 0.1% |
| water | QS |
| External phase | |
| magnesium stearate | 1% |
| wherein the sodium alkylsulfate is incorporated in step b). | |

9. A process according to claim 6 for the preparation of a pharmaceutical composition in the form of a gelatin capsule and having the following formulation, expressed in percentages by weight:

| Internal phase | |
|---|---|
| N-piperidino-5-(4-chlorophenyl)-1-(2,4-dichlorophenyl)-4-methylpyrazole-3-carboxamide in micronized form | 17.64% |
| corn starch | 30% |
| 200 mesh lactose monohydrate | 43.73% |
| povidone K 30 | 2.53% |
| crosslinked sodium carboxymethyl cellulose | 5% |
| Granulation | |
| sodium laurylsulfate | 0.1% |
| water | QS |
| External phase | |
| magnesium stearate | 1% |
| wherein the sodium alkylsulfate is incorporated in step b). | |

10. A pharmaceutical composition according to claim 1 wherein the sodium alkylsulfate is added to purified water for wet granulation.

11. A pharmaceutical composition according to claim 2 wherein the sodium alkyl sulfate is added to purified water for wet granulation.

12. A pharmaceutical composition according to claim 1 in the form of gelatin capsules, tablets, sachets or powders.

13. A pharmaceutical composition according to claim 2 in the form of gelatin capsules, tablets, sachets or powders.

* * * * *